(12) United States Patent
Ryoichi

(10) Patent No.: US 6,911,213 B2
(45) Date of Patent: Jun. 28, 2005

(54) PERNASALLY ABSORBABLE INSULIN PREPARATIONS

(75) Inventor: Nagata Ryoichi, Kagoshima (JP)

(73) Assignee: Translational Research Ltd., Kagoshima (JP)

(*) Notice: Subject to any disclaimer, the term of this patent is extended or adjusted under 35 U.S.C. 154(b) by 0 days.

(21) Appl. No.: 10/019,396

(22) PCT Filed: Apr. 26, 2001

(86) PCT No.: PCT/JP01/03642
§ 371 (c)(1),
(2), (4) Date: Dec. 28, 2001

(87) PCT Pub. No.: WO01/82950
PCT Pub. Date: Nov. 8, 2001

(65) Prior Publication Data
US 2003/0082240 A1 May 1, 2003

(30) Foreign Application Priority Data
May 2, 2000 (JP) .......................... 2000-133289

(51) Int. Cl.⁷ .............................................. A61F 13/00
(52) U.S. Cl. ...................................... 424/434; 424/422

(58) Field of Search ................................. 424/422, 434

(56) References Cited

U.S. PATENT DOCUMENTS 5,948,438 A * 9/1999 Staniforth et al. .......... 424/464
6,197,328 B1 * 3/2001 Yanagawa

FOREIGN PATENT DOCUMENTS

| EP | 0 681 833 A2 | * 4/1995 | |
| EP | 681 833 | 11/1995 | |
| EP | 0 681 833 A2 | * 11/1995 | ............ A61K/9/14 |
| JP | 8-27031 | 1/1996 | |
| JP | 11-322582 | 11/1999 | |

* cited by examiner

Primary Examiner—Thurman K. Page
Assistant Examiner—Humera N. Skeikh
(74) Attorney, Agent, or Firm—Wenderoth, Lind & Ponack, L.L.P.

(57) ABSTRACT

An insulin formulation with porous, spherical calcium carbonate composed of trabeculate or needle-shaped crystals, or an aggregation of the parallel intergrowth of these forms, as its carrier, will be presented. This formulation is beneficial for the treatment of diabetes.

8 Claims, 3 Drawing Sheets

×100

×1,000

×10,000

×100

×1,000

×10,000

PERNASALLY ABSORBABLE INSULIN PREPARATIONS

TECHNICAL FIELD

The present invention concerns a formulation for the nasal absorption of insulin. Specifically, it concerns a formulation using calcium carbonate particles of specific structure as insulin carriers and a method for treating diabetes

BACKGROUND ART

In the treatment of diabetes, insulin is presently administered by injection. Particularly, subcutaneous self-injection, a comparatively simple method, has been the major route of administration. However, patients are obliged to inject themselves before meal once to four times a day throughout their lives, and the discomfort accompanying injection is a major disadvantage of this method of treating diabetes.

Conversely, intranasal administration is known to be route that enables drugs to be rapidly absorbed post dosing. However, no insulin formulation for intranasal administration has been available for clinical use, due to poor absorbability and stability through/in the nasal cavity. Moreover, numerous preparations using absorption enhancers to improve the nasal absorbability of insulin have been impracticable because of irritation of the nasal mucosa.

JP-A-8-27031 presented a formulation for nasal absorption comprising a drug selected from a variety of drugs including physiologically active peptides such as insulin and calcitonin, and a polyvalent metallic compound as a carrier, which drug is uniformly dispersed on, adhered and binding to the carrier. According to this publication, it is suggested that, for example, the use of hydroxyapatite, calcium carbonate, calcium lactate, and magnesium stearate as carriers with an average particle diameter of 30–60 $\mu$m, enable insulin to be efficiently delivered into the systemic circulation. The application of hydroxyapatite with a particle diameter of 40–45 $\mu$m, as a carrier for nasal insulin absorption is comprehensively described in this publication, embodying account of an in vivo study that demonstrated the blood glucose level (blood-sugar level) after intranasal administration using the said formulation decreased in similar manner to that after subcutaneous administration.

The formulation for nasal absorption described in the above-mentioned JP-A-8-27031 has achieved a specific aim and is extremely beneficial. However, there is a great demand for a further optimized formulation (e.g. improved bioavailability) for nasal absorption.

Accordingly, the purpose of this invention is to provide a further optimized formulation for the nasal absorption of insulin that to enables high bioavailability.

DISCLOSURE OF THE INVENTION

To attain this aim, the present inventor investigated the effect of combinations of insulin and various carriers on the nasal absorption of insulin and, thereby the use of a specific calcium carbonate structure for intranasal insulin delivery was found to significantly increase blood insulin levels and significantly decrease blood-sugar levels.

The present invention was derived from the above-mentioned findings.

Accordingly, the present invention provides a formulation for the nasal absorption of insulin comprising a component composed of insulin and porous, spherical calcium carbonate as its carrier. In addition, the present invention provides a formulation for nasal absorption of insulin comprising a component composed of insulin and calcium carbonate as its carrier, in which said calcium carbonate comprises cubic or trigonal crystals (specifically originating from a pharmacopeial product), with a particle diameter in the range of 20–32 $\mu$m.

The present invention also provides, as another aspect, a method for the treatment of diabetes which comprises administering a component composed of insulin and porous, spherical calcium carbonate as its carrier into the nasal cavities of diabetics who need administration of an effective amount of insulin.

Additionally, the present invention provides, as another aspect, the use of a component composed of insulin and porous, spherical calcium carbonate as its carrier, to prepare a formulation for the nasal absorption of insulin.

BEST MODE FOR CARRYING OUT THE INVENTION

Any form of modified or unmodified insulin used in treating diabetes in humans may be used with the invention, regardless of its origin. Accordingly, any human insulin, swine-derived refined insulin, semi-synthetic human insulin, human isoinsulin, etc. or any other human insulin obtainable by gene manipulation technology that has an activity similar to that of human insulin can be used as "insulin" with the present invention.

The calcium carbonate to be used as a carrier is either porous and spherical in form or substantially composed of cubic or trigonal crystals with a particle diameter in the range of 20–32 $\mu$m.

Figure 1:
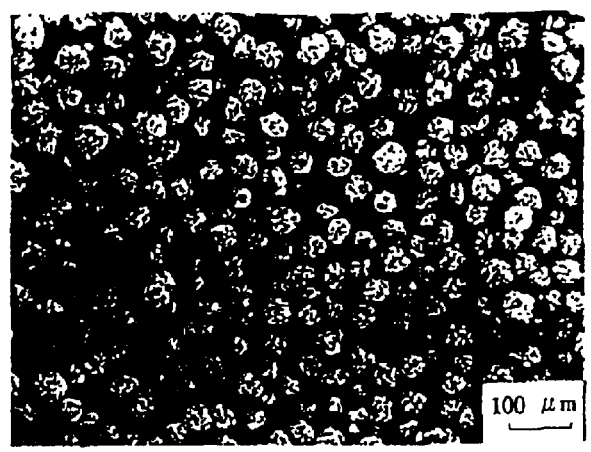
FIG. 1 shows photomicrographs of porous, spherical calcium carbonate utilizable as a carrier in a formulation of the present invention.
Figure 1:
Figure 1:
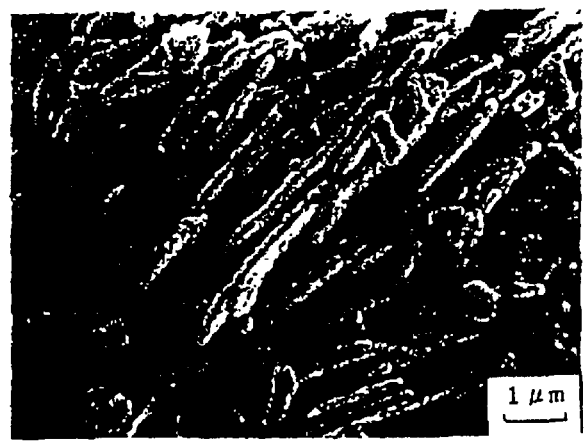

The above-mentioned term "porous spherical", as may be seen in FIG. 1, which shows an example of porous spherical calcium carbonate, means an aggregation of trabeculate or needle-shaped crystalline, or a parallel intergrowth of these, and the substantial form is spherical. Parallel intergrowth means a state of growth in which two or more crystals grow in parallel along a certain crystalline axis. It can be assumed that these crystals, or a larger number, converge to form a spherical entity, and thus the constituent particles become porous.

The porous, spherical calcium carbonate has a particle diameter in the substantial range of 18–115 $\mu$m. "Substantial range" herein means the range in which the same nature or behavior as that of an ideal particle is observed or is shown by all particles (100%). For instance, when the word "substantial" is used in relation to the range of particle diameter, it means that at least 70%, or preferably at least 90%, of related particles show a particle diameter within a specific range. The desirable particle diameter of the porous, spherical calcium carbonate in question is within the substantial range of 20–32 µm, while preferably, 100% of related particles should be within this range. In addition to the particle diameter being within the above-mentioned range, it is particularly desirable that the median particle diameter be 22 µm or greater and less than 30 µm.

Moreover, although not a porous sphere as described above, calcium carbonate with a particle diameter in the above-mentioned desirable range, such as a cubic or trigonal calcium carbonate crystal obtained from a classified, pharmacopeial product, even though principally calcite in form, will act as a significantly superior insulin carrier in comparison with calcium carbonate crystals of an identical nature with a particle diameter of 40–45 µm or greater.

Porous, spherical calcium carbonate with a particle diameter within the desirable range can be synthesized by a recognized method and, depending on the required classification, may be used in the present invention. In the context of the present invention, light calcium carbonate means a synthetic product. Synthetic calcium carbonate is generally produced by the calcination of limestone followed by recarbonization by aeration. In the course of such manufacture, any necessary additive that can promote or control the reaction may be used, and the process may be further controlled by regulation of the reaction temperature and agitation in order to synthesize desired forms of calcium carbonate. It is understandable, therefore, that synthetic calcium carbonate produced by this process for use in the present invention may contain magnesium and alkaline metals etc., on condition that these satisfy pharmacopeial requirements.

Table 1 shows an example of the distribution of porous, spherical calcium carbonate particle size that can be used in connection with the present invention, including those of a certain particle diameter that are classifiable.

TABLE 1

| No. | Particle size X (µm) | Distribution (%) |
| --- | --- | --- |
| 1 | 171 | 0 |
| 2 | 140 | 0 |
| 3 | 114 | 0.20 |
| 4 | 94 | 0.65 |
| 5 | 77 | 1.95 |
| 6 | 62 | 9.75 |
| 7 | 50 | 35.50 |
| 8 | 40 | 38.20 |
| 9 | 35 | 10.95 |
| 10 | 28 | 1.95 |
| 11 | 23 | 0.62 |
| 12 | 18 | 0.23 |
| 13 | 15 | 0 |
| 14 | 12 | 0 |
| 15 | 10 | 0 |

The calcium carbonate used in connection with the present invention is characterized by having a relative surface area of 1.5 m$^2$/g or greater (BET method). This is significantly higher than that of standard light calcium carbonate available on the market, which is usually 0.1–0.3 m$^2$/g.

This calcium carbonate, or a classified product obtained through an appropriate sieve, may be combined, as a carrier, with any quantity of insulin as long as the insulin can be adsorbed or carried as a monolayer or multilayer. As a general rule, however, insulin can be combined within the range of 0.1–50%, but preferably 1–10%, of the total weight of a combined component. Said component can be prepared by malaxation of insulin and calcium carbonate with an appropriate quantity of water using a suitable malaxation apparatus, and subsequent freeze-drying.

The component may be used intact as for a formulation for the nasal absorption of insulin, as described in the present invention. Alternatively, when or after preparing said formulation, any mucosal absorption enhancer, stabilizer, preservative, etc. is can be combined with the formulation of the present invention with no negative effects It is advisable to store such formulations intact or in capsules in an airtight package. The formulation of the present invention for the nasal absorption of insulin obtained through the processes described above, therefore, provides significantly enhanced pharmacokinetic characteristics (e.g. maximum blood concentration, area under blood concentration curve, bioavailability). Known devices for nasal medication, including nasal sprays, can be used for nasal administration.

Dose levels are not specified, because they will vary according to medical condition, age, body weight etc; however, it is preferable that they should be set by a medical specialist in reference to information such as the pharmacokinetic parameters of cynomolgus monkeys as stated below.

Formulations for the nasal absorption of the present invention obtained through the procedures described above have not shown any toxicity greater than that of subcutaneously injected Novolin (trademark), a recombinant human insulin manufactured by Novo Nordisk A/S.

The following is a detailed description of a practical example of the present invention, referring to the study of a formulation for the nasal absorption of insulin using the present invention. It is not intended that this description should limit the use of the present invention to such an example. The insulin used in the invention is recombinant human insulin obtained from Novo Nordisk A/S.

Pharmacokinetic and Pharmacodynamic Study using Cynomolgus Monkeys

Unless otherwise specified, 3–18 male cynomolgus monkeys per group (weighing 2–7 Kg) each received a single nasal administration of the formulation under study. Blood insulin and serum glucose concentrations of each animal were examined chronologically.

Insulin and glucose concentrations were measured by EIA (Enzyme Immune Assay) and GlcKG-6-PDH, respectively.

Each preparation was encapsulated and administered intranasally using an intranasal administration device (Jetlizer, Unisia Jecs Co.,Ltd.).

(1) Cynomolgus monkeys received a formulation composed of insulin and porous, spherical calcium carbonate [particle diameter: 20–32 µm (hereinafter "PSCaCO$_3$, 20–32 µm")], or cubic calcium carbonate derived from a pharmacopeial product [particle diameter: 20–32 µm (hereinafter "CaCO$_3$, 20–32 µm")], or for comparison, cubic calcium carbonate derived from a pharmacopeial product [particle diameter: 10–180 µm (hereinafter "CaCO$_3$, 10–180 µm")] or Novolin R40 (trademark) administered by subcutaneous administration. The results determining pharmacokinetic parameters (mean±S.E.) of serum insulin are shown below in Table 2.

Figure 2:
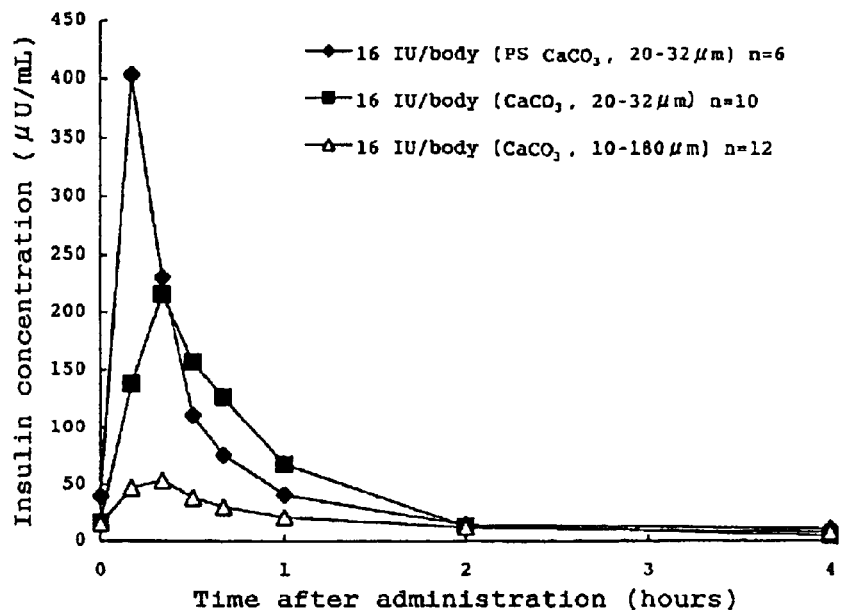
FIG. 2 is a graph showing serum insulin concentrations following intranasal administration of each formulation to cynomolgus monkeys.
Figure 3:
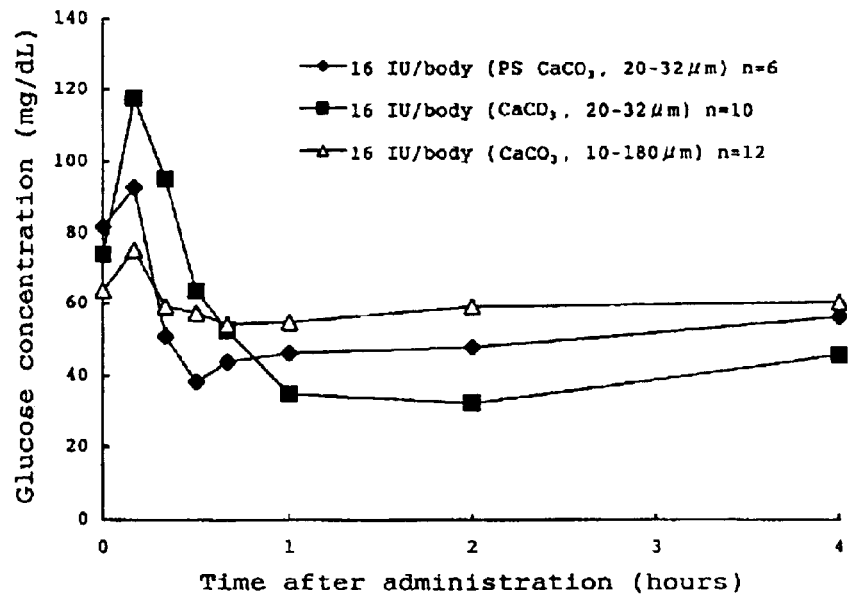
FIG. 3 is a graph showing serum glucose concentrations following intranasal administration of each formulation to cynomolgus monkeys.

FIGS. 2 and 3 show serum insulin concentration-time curves and serum glucose concentration-time curves, respectively, for the above-mentioned formulations for nasal absorption.

TABLE 2

| Formulation | Formulation Of Spherical Calcium Carbonate (PSCaCO$_3$ 20–32 μm) | Formulation Of Cubic Calcium Carbonate (CaCO$_3$ 20–32 μm) | Formulation Of Cubic Calcium Carbonate (CaCO$_3$ 10–180 μm) | Novolin R 40 |
|---|---|---|---|---|
| No. animal | 6 | 10 | 12 | 12 |
| Dosing route | Nasal | Nasal | Nasal | Subcutaneous |
| Dose (IU/body) | 16 | 16 | 16 | 0.5 |
| $C_{max}$ (IU/mL) | 403.47 ± 43.60 | 218.22 ± 28.93 | 58.86 ± 7.15 | 103.06 ± 14.42 |
| $t_{max}$ (h) | 0.17 ± 0.00 | 0.36 ± 0.03 | 0.28 ± 0.02 | 0.29 ± 0.04 |
| $t_{1/2}$ (h) | 1.02 ± 0.18 | 0.68 ± 0.04 | 2.18 ± 0.92 | 0.98 ± 0.13 |
| $AUC_{0-4}$ (μU·h/mL) | 206.85 ± 17.71 | 187.86 ± 32.38 | 72.38 ± 8.95 | 113.67 ± 13.71 |
| MRT(h) | 0.78 ± 0.07 | 0.92 ± 0.05 | 1.27 ± 0.08 | 1.09 ± 0.09 |
| Comparative Bioavailability (%) | 5.69 | 5.17 | 2.00 | 100.00 |

As shown in Table 2, intranasal administration of 16 IU of insulin per animal using PSCaCO$_3$20–32 μm or CaCO$_3$20–32 μm (both derived from the present invention) as a carrier, demonstrated significantly greater bioavailability than that using CaCO$_3$ (non-porous and non-spherical calcium carbonate, particle diameter: 10–180 μm). Furthermore, PSCaCO$_3$20–32 μm demonstrated that bioavailability and $C_{max}$ values approximately 1.1 and 1.8 times, respectively, greater than those of CaCO$_3$20–32 μm, further demonstrating enhanced bioavailability (Refer to FIG. 2). The raw data relating to FIG. 2 are shown in Table 3–5, corresponding to PSCaCO$_3$20–32 μm, CaCO$_3$20–32 μm and CaCO$_3$10–180 μm, respectively.

Figure 4:
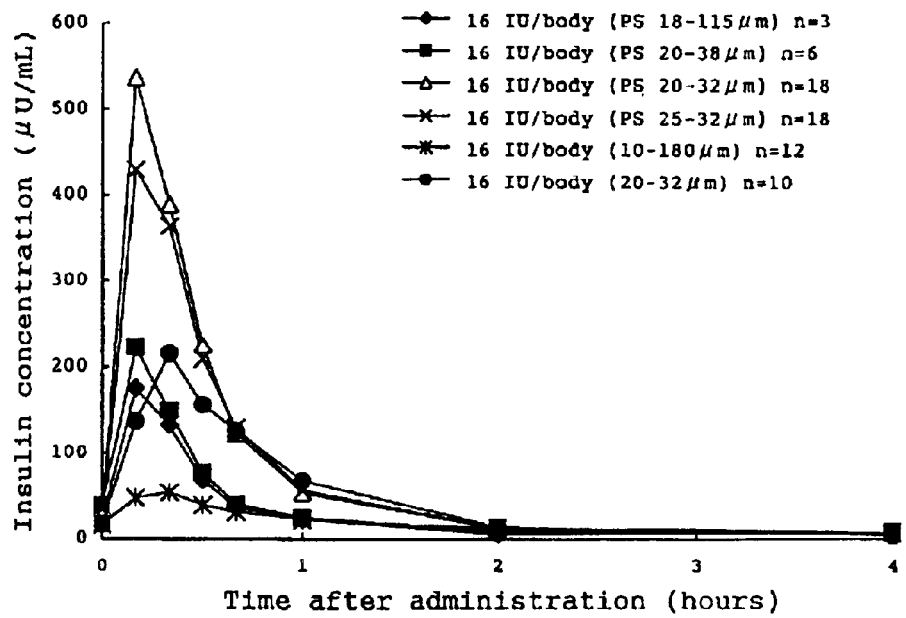
FIG. 4 is a graph showing serum insulin concentrations following administration of each formulation to cynomolgus monkeys.
Figure 5:
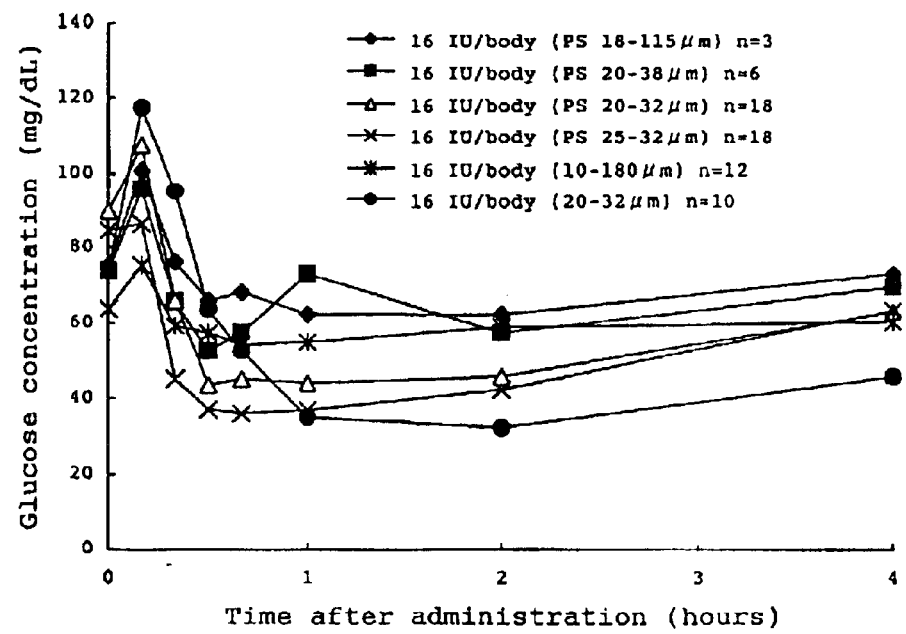
FIG. 5 is a graph showing serum glucose concentrations following administration of each formulation to cynomolgus monkeys.

(2) In the same manner as described above, cynomolgus monkeys received intranasal administrations of insulin formulations (16 IU of insulin per animal) intranasally using porous, spherical calcium carbonate [particle diameter: 18–115 μm (hereinafter "PSCaCO$_3$18–115 μm"), particle diameter: 20–38 μm (hereinafter "PSCaCO$_3$20–38 μm"), particle diameter: 20–32 μm (hereinafter "PSCaCO$_3$20–38 μm"), particle diameter: 20–32 μm (hereinafter "PSCaCO$_3$20–32 μm"), particle diameter: 25–32 μm (hereinafter "PSCaCO$_3$25–32 μm")] or cubic calcium carbonate derived from a pharmacopeial product [particle diameter: 20–32 μm (hereinafter "CaCO$_3$20–32 μm"), particle diameter: 10–180 μm (hereinafter "CaCO$_3$10–180 μm")] as a carrier, and serum insulin and serum glucose concentrations were examined chronologically. The results are shown in FIGS. 4 and 5.

TABLE 3

| Animal No. | Insulin (μU/mL) | | | | | | | |
|---|---|---|---|---|---|---|---|---|
| | 0 | 10 min | 20 min | 30 min | 40 min | 1 hr | 2 hr | 4 hr |
| 1 | 36.2 | 425.6 | 229.7 | 125.0 | 73.2 | 33.6 | 9.0 | 13.2 |
| 2 | 31.7 | 494.4 | 332.4 | 156.1 | 121.4 | 56.7 | 13.3 | 2.7 |
| 3 | 22.3 | 263.6 | 164.4 | 82.2 | 59.9 | 37.7 | 16.7 | 6.8 |
| 4 | 59.5 | 321.6 | 220.4 | 101.0 | 72.6 | 60.7 | 26.7 | 23.7 |
| 5 | 31.4 | 367.8 | 124.5 | 97.8 | 66.4 | 29.3 | 7.6 | 4.8 |
| 6 | 58.8 | 547.6 | 310.4 | 102.1 | 60.1 | 28.5 | 13.9 | 16.9 |
| Mean | 39.98 | 403.47 | 230.30 | 110.70 | 75.60 | 41.08 | 14.53 | 11.35 |
| S.D. | 15.52 | 106.81 | 80.59 | 26.12 | 23.17 | 14.09 | 6.83 | 8.06 |

TABLE 4

| Animal No. | Insulin (μU/mL) | | | | | | | |
|---|---|---|---|---|---|---|---|---|
| | 0 | 10 min | 20 min | 30 min | 40 min | 1 hr | 2 hr | 4 hr |
| 1 | 13.3 | 181.2 | 275.6 | 224.5 | 214.6 | 115.2 | 27.2 | 6.7 |
| 2 | 29.2 | 237.8 | 294.0 | 198.0 | 123.6 | 47.2 | 8.7 | 3.5 |
| 3 | 13.7 | 175.7 | 236.8 | 156.6 | 84.6 | 72.2 | 11.3 | 4.6 |
| 4 | 13.4 | 224.3 | 344.6 | 305.6 | 291.8 | 203.0 | 28.9 | 4.3 |
| 5 | 20.8 | 69.2 | 145.1 | 93.4 | 74.9 | 33.5 | 8.5 | 4.4 |
| 6 | 13.7 | 30.7 | 67.6 | 60.9 | 94.9 | 38.2 | 5.9 | 1.3 |
| 7 | 9.0 | 134.7 | 214.8 | 115.4 | 72.4 | 27.2 | 4.3 | 2.9 |
| 8 | 19.2 | 39.0 | 125.4 | 82.6 | 84.7 | 41.1 | 13.8 | 5.3 |
| 9 | 31.1 | 121.5 | 123.8 | 71.7 | 62.6 | 28.9 | 4.2 | 4.1 |
| 10 | 6.5 | 163.7 | 327.2 | 262.4 | 160.1 | 67.9 | 23.3 | 7.1 |
| Mean | 16.99 | 137.78 | 215.49 | 157.07 | 126.42 | 67.44 | 13.61 | 4.42 |
| S.D. | 8.09 | 72.79 | 95.88 | 86.37 | 74.83 | 54.67 | 9.44 | 1.71 |

TABLE 5

| Animal No. | Insulin (μU/mL) | | | | | | | |
|---|---|---|---|---|---|---|---|---|
| | 0 | 10 min | 20 min | 30 min | 40 min | 1 hr | 2 hr | 4 hr |
| 1 | 21.0 | 54.5 | 65.2 | 45.1 | 30.5 | 28.4 | 37.5 | 8.6 |
| 2 | 21.7 | 85.8 | 111.7 | 68.2 | 70.4 | 37.8 | 15.8 | 14.7 |
| 3 | 21.9 | 16.0 | 46.3 | 27.0 | 12.9 | 21.6 | 6.1 | 8.9 |
| 4 | 34.0 | 42.8 | 76.0 | 46.6 | 46.2 | 24.3 | 6.6 | 11.8 |
| 5 | 7.8 | 25.0 | 20.3 | 13.7 | 8.8 | 6.1 | 2.9 | 2.5 |
| 6 | 5.6 | 45.3 | 58.9 | 46.5 | 30.9 | 19.2 | 5.9 | 1.9 |
| 7 | 29.9 | 54.7 | 19.9 | 33.8 | 40.7 | 32.0 | 27.6 | 6.9 |
| 8 | 4.8 | 40.1 | 44.5 | 34.0 | 23.5 | 15.1 | 6.1 | 2.2 |
| 9 | 16.5 | 28.8 | 19.2 | 18.2 | 12.9 | 9.7 | 21.5 | 14.3 |
| 10 | 2.1 | 61.2 | 45.1 | 32.5 | 27.5 | 14.6 | 4.4 | 1.8 |
| 11 | 15.8 | 39.8 | 44.0 | 32.9 | 25.3 | 28.9 | 6.8 | 7.9 |
| 12 | 7.7 | 71.8 | 90.0 | 66.4 | 40.1 | 23.0 | 4.4 | 12.2 |
| Mean | 15.73 | 47.15 | 53.43 | 38.74 | 30.81 | 21.73 | 12.13 | 7.81 |
| S.D. | 10.32 | 19.85 | 28.75 | 16.79 | 17.08 | 9.33 | 11.12 | 4.84 |

Each table, FIGS. 2 and 4, and in particular FIG. 4, show that formulations for nasal absorption based on the present invention, i.e., PSCaCO$_3$20–32 μm, PSCaCO$_3$20–38 am, PSCaCO$_3$ 25–32 μm, PSCaCO$_3$18–115 μm and CaCO$_3$20–32 μm increase serum insulin concentrations significantly in comparison with CaCO$_3$10–180 μm.

INDUSTRIAL APPLICABILITY

The formulations for the nasal absorption of insulin in the present invention are beneficial in the treatment of diabetes, which requires the administration of insulin, because it increases serum insulin concentration without unacceptable irritation. Accordingly, it is available in industries such as pharmaceutical production.

What is claimed is:

1. A formulation for the nasal absorption of insulin, which comprises a component composed of insulin and porous, spherical calcium carbonate as its carrier, said calcium carbonate having a relative surface area of 1.5 $m^2/g$ or greater (BET method) and the porous, spherical calcium carbonate has a particle diameter substantially in the range of 20–32 $\mu$m, wherein the insulin is adsorbed or carried on said carrier as a monolayer or multilayer.

2. The formulation according to claim 1, in which the porous, spherical calcium carbonate, comprises trabeculate or needle-shaped crystals, or an aggregation of the parallel intergrowth of these forms.

3. The formulation according to claim 1, in which the porous, spherical calcium carbonate has a particle diameter substantially in the range of 20–32 $\mu$m, and a median particle diameter of 22 $\mu$m or greater and less than 30 $\mu$m.

4. The formulation according to claim 1, in which the insulin content of the component composed of insulin and porous, spherical calcium carbonate is 0.1–50% by weight based on the total weight of the component.

5. The formulation for the nasal absorption of insulin comprising a component composed of insulin and calcium carbonate as its carrier, in which the calcium carbonate is substantially composed of cubic or trigonal system crystals and has a particle diameter in the range of 20–32 $\mu$m.

6. The formulation according to claim 1, in which the insulin content of the component composed of insulin and calcium carbonate is 0.1–50% by weight based on the total weight of the component.

7. A method for the treatment of diabetes that comprises administering the formulation of claim 1 into the nasal cavities of diabetics who need an effective amount of insulin.

8. The method according to claim 7, in which the calcium carbonate is substantially composed of cubic or trigonal system crystals with a particle diameter in the range of 20–32 $\mu$m, and the insulin content of a combined component of insulin and calcium carbonate is 0.1–50% by weight based on the total weight of the component.

* * * * *